(12) United States Patent
Ames

(10) Patent No.: US 6,361,983 B1
(45) Date of Patent: Mar. 26, 2002

(54) PROCESS FOR THE ISOLATION OF 1,3-PROPANEDIOL FROM FERMENTATION BROTH

(75) Inventor: Tyler T. Ames, Newark, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/671,931

(22) Filed: Sep. 27, 2000

Related U.S. Application Data

(60) Provisional application No. 60/156,875, filed on Sep. 30, 1999.

(51) Int. Cl.[7] ............... C12P 7/18; C12P 7/64; C12P 7/20; C07C 29/74; C07C 31/18; C07C 27/04; C07C 27/26
(52) U.S. Cl. ............ 435/158; 435/134; 435/159; 568/810; 568/852; 568/862; 568/868
(58) Field of Search ............... 568/868, 810, 568/852, 862; 435/134, 158, 159

(56) References Cited

U.S. PATENT DOCUMENTS 5,177,008 A * 1/1993 Kampen ............ 435/139
5,527,973 A    6/1996 Kelsey ............. 568/862

OTHER PUBLICATIONS

Barantsev et al., *Fermentn. Spirit. Prom–st. 2:24–27 (1976)* (Abstract).

* cited by examiner

*Primary Examiner*—Samuel Barts
*Assistant Examiner*—Elvis O. Price

(57) ABSTRACT

The invention concerns a process for the isolation of polyols, such as 1,3-propanediol, from a fermentation broth. Specifically, the invention discloses a process of adding base to the fermentation broth to raise the pH to a suitable level for reduction of impurity formation during isolation of the polyol.

2 Claims, 6 Drawing Sheets

US 6,361,983 B1

PROCESS FOR THE ISOLATION OF 1,3-PROPANEDIOL FROM FERMENTATION BROTH

This application claims benefit of Prov. No. 60/156,875 filed Sep. 30, 1999.

FIELD OF THE INVENTION

This invention relates to a process for the isolation of polyols from a fermentation source. Specifically, this invention relates to a process for the isolation of 1,3 propanediol from a fermentation source.

BACKGROUND OF THE INVENTION

Polyols are compounds that contain two or more hydroxyl groups. 1,3-Propanediol is one example of a polyol. 1,3-Propanediol is a precursor for several polymeric materials including polyether polyols, polyester homopolymers and copolymers, and thermoplastic elastomers. 1,3-Propanediol is commercially produced via chemical synthesis routes including (a) ethylene oxide hydroformylation followed by hydrogenation, and (b) hydration of acrolein followed by hydrogenation. Both routes rely on petroleum based feedstocks. Purification of petroleum-based 1,3-propanediol requires significant effort as the quality of the aforementioned polymeric products is generally dependent on the quality of the monomers.

Alternatively, 1,3-propanediol can be produced from processing of renewable agricultural resources which yield fermentable sugars, especially glucose. Glucose can be converted to 1,3-propanediol via a single biocatalyst, yielding an aqueous fermentation broth containing many residual medium components and byproducts. Fermentation residuals and byproducts are in general different from impurities found in chemical synthesis. Inherent in biological systems utilizing agricultural feedstocks, is greater variability in composition of product than obtained with chemical synthesis from petroleum feedstocks. Furthermore, fermentation residuals and byproducts in general encompass a wider range of structures and physical properties than chemical synthesis byproducts. Isolation and purification of 1,3-propanediol from a fermentation source therefore has significant and unmet challenges above that of processes which produce 1,3-propanediol via chemical synthesis.

U.S. Pat. No. 5,527,973 discloses a process for purifying a carbonyl-containing 1,3-propanediol composition. The process involves formation of an acidic aqueous medium, addition of a base to raise the pH to greater than 7, distillation of the solution to remove water, and subsequent distillation of the 1,3-propanediol yielding a product with lower carbonyl content than the starting composition. This disclosure does not address 1,3-propanediol produced via a fermentation process, nor byproducts and impurities specific to a fermentation process, nor byproducts formed during isolation and purification of such a material. Examples outside the scope of this disclosure include organic acids, proteins, inorganic salts, lactones, nitrogen heterocycals, and color bodies.

Separation and purification of chemicals produced by fermentation are driven both by the nature of the product and the nature of a typical fermentation broth. Fermentations may typically produce a broth which contains only a 1 to 10% concentration of the desired product. Furthermore, the broth contains biomass and a wide variety of other constituents potentially including but not limited to: proteins, amino acids, lipids, organic acids, organic and inorganic salts, and residual medium nutrients. Two common steps in processing of broth are therefore removal of biomass, and isolation of the product from the highly dilute system. Biomass removal may typically be done by filtration or centrifugation. A wide variety of isolation methods are available including filtration, evaporation, extraction, and crystallization. After isolation step(s), the product may be expected to be the major component, with impurities comprising a smaller fraction of the composition. If deemed necessary, purification involves removal of impurities to the degree required for an acceptable product.

Barantsev et al. (Fermentn. Spirt. Prom-st. 2:24–27 (1976)) disclose a method for reducing the quantities of impurities formed and improving distillate quality in alcohol distillation. The distillation feed was molasses fermented mashes, which was reported to produce impurities from interaction of alcohols, acids, aldehydes, and amino acids. Improvements were made by raising pH, and reducing the pressure and therefore the distillation temperature. This study does not address the conditions required for processing polyols in general, and more specifically 1,3-propanediol. Atmospheric distillation of ethanol and 1,3-propanediol would occur at 78 and 214° C., respectively. While distillation at a vacuum of 50 mmHg would reduce the ethanol distillation to 22° C., and 1,3-propanediol distillation would operate at 137° C. Therefore, the energy available for reaction activation is significantly different and greater for 1,3-propanediol processing. Barantsev does not consider glycol dehydration reactions, or more specifically 1,3-propanediol dehydration reactions. In addition, Barantsev does not consider a process where water is removed as a vapor, and the product which has a higher boiling point remains in the liquid phase as "bottoms" or "heel". The process does not address abatement of impurities which are either known or believed to be unique to 1,3-propanediol processing. Furthermore, Barantsev does not disclose a pH which is optimal for processing 1,3-propanediol produced by fermentation or consider color of purified 1,3-propanediol.

A method to isolate polyols produced by fermentation processes without the deficiencies discussed above remains a problem to be solved. More specifically, a process for the isolation of 1,3-propanediol from fermentation is needed.

SUMMARY OF THE INVENTION

The present invention discloses a process for the isolation of polyol(s) from a fermentation broth comprising the steps of:

(a) adding base to the fermentation broth to raise the pH to at least 7.0; and (b) isolating the polyol from the fermentation broth of step (a).

Polyols of particular interest in the invention are 1,3-propanediol, 1,2-propanediol, 1,4-butanediol, glycerol, or ethylene glycerol. Isolating in step (b) is by evaporating, distilling, filtering, extracting, or crystallizing. After step (c) the invention may further include removing precipitated solids from the product of step (b) by 1) filtering or centrifuging, or 2) vacuum distilling.

BRIEF DESCRIPTION OF THE DRAWINGS

The instant invention is further elucidated with reference to the figures, where.

DETAILED DESCRIPTION OF THE INVENTION

Figure 1:
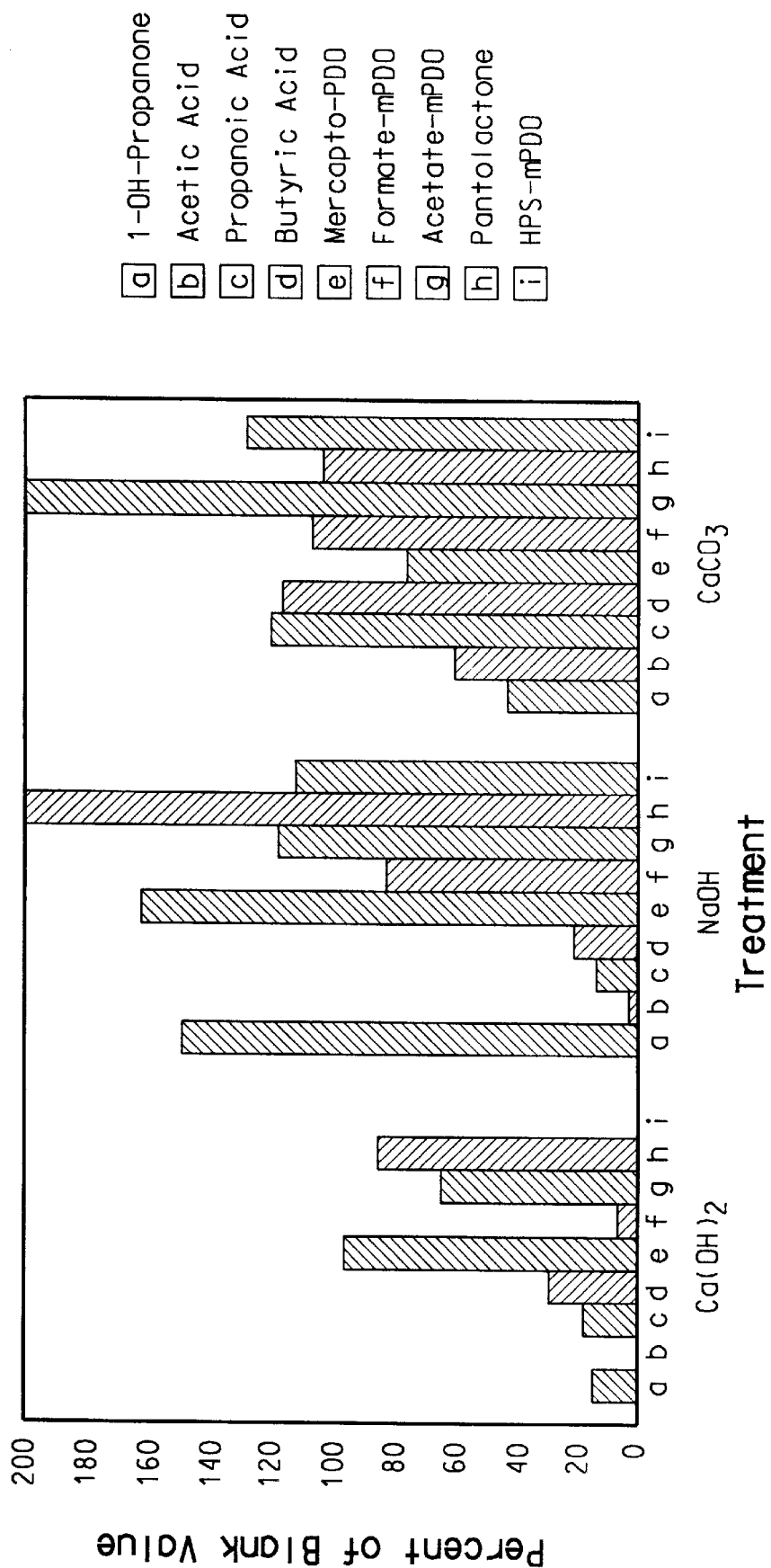
FIG. 1 illustrates an analysis of partially evaporated broth impurities via gas chromatography.

The present invention provides a process by which polyols produced by fermentation are isolated. Specifically, the present invention provides a process by which 1,3-propanediol produced by fermentation is isolated. The instant invention discloses a process of adding base to the fermentation broth to raise the pH to a suitable level for reduction of impurity formation during isolation of the polyol.

In addition, the invention discloses a method for removing water from the fermentation broth by evaporation and distillation, and the de-watered 1,3-propanediol is further purified by distillation. The first step is to adjust the broth with a base to a pH which is adequate to prevent by-product formation during evaporation. More preferably, the base is one which leads to significant precipitation of dissolved solids in the second step, allowing separation from the concentrated 1,3-propanediol. The second step is isolating the polyol from the fermentation broth. One method for isolation is by thermal evaporation of a major portion of the water, producing a more concentrated 1,3-propanediol. More preferably, precipitated solids are then removed from the concentrated 1,3-propanediol by filtrating or centrifuging. Another method to isolate the polyol is removing the remaining water and dissolved solids by vacuum distillation. This step may be accomplished in one, but likely more than one distillations. There may be further addition of base prior to distillation if the amount added in step one was not sufficient to result in a pH which prevents or reduces by-product and color formation during distillation. Additionally, removal of remaining impurities from the 1,3-propanediol may be by vacuum distillation. Again, this process may be accomplished in one, but likely more than one distillations. There may also be further addition of base prior to distillation if the amount added previously was not sufficient to result in a pH which prevents or reduces by-product and color formation during distillation. Adding base may also be done initially, during the isolating methods, or as part of a process control system designed to maintain pH at a chosen level.

The following abbreviations and definitions will be used for the interpretation of the specification and the claims.

"1,3-Propanediol" is abbreviated PDO.

"3-Hydroxy-propionic acid ester of 1,3-propanediol" is abbreviated HPS-mPDO.

"Formic acid ester of 1,3-propanediol" is abbreviated formate-mPDO.

"Polyol" refers to an organic compound containing two or more hydroxyl groups. Examples of polyols are 1,3-propanediol, 1,2-propanediol, 1,4-butanediol, glycerol, and ethylene glycol.

"Isolation" refers to separating the polyol from the fermentation broth using available methods such as evaporation, distillation, filtration, extraction and crystallization.

The composition of fermentation broth containing 1,3-propanediol described in the examples of this invention undergo changes during isolation and purification, resulting in a decrease in pH. While not wishing to be bound by any mechanism, the Applicant believes that ammonium present in the fermentation broth is liberated as ammonia which is readily lost as a gas when the broth is subjected to heating and/or vacuum treatment. As such a system must be ionically balanced, one mole of $H^+$ is left in solution for every mole of $NH_3$ liberated. In other words, ammonium salts of organic and mineral acids are converted to free organic and mineral acids, reducing the broth pH. Isolating and purifying 1,3-propanediol under such acidic conditions has been found to result in formation of by-products and color. 1,3-Propanediol isolated and purified under such acidic conditions has been found to be unsuitable for producing good quality, color-free polyester. Several of the impurities formed are known to be derivatives of 1,3-propanediol, resulting in yield losses and unfavorable economics for a manufacturing process. Some impurities produced under the acidic conditions (such as 1,3-propanediol-esters of the organic fermentation acids) would be expected by one familiar with similar art. However, other impurities could not be anticipated. Likewise, abatement of expected impurity formation via increased pH may be expected, but abatement of non-anticipated impurities would not. Furthermore, the nature and composition of color formed during processing is not established, and therefore could not be expected to be abated by base addition or increase of pH.

Adding base in the isolation and purification process effects the pH as well as the nature and composition of ionic species in solution and precipitated as solids. The base may be strong or weak, inorganic or organic in nature, while satisfying the condition of not contributing to impurity formation due to decomposition, action as a catalyst, or other mechanisms. More preferably, the base forms salts of limited or negligible solubility with ions in the fermentation broth. This result may be achieved by: strong bases with divalent cations such as calcium hydroxide, strong bases with trivalent cations such as aluminum hydroxide, weak bases with multivalent cations such as calcium carbonate, and weak organic bases such as hexamethylenediamine. The amount of base added must be sufficient to maintain a pH of equal to or greater than 7. More preferably, the amount of base added will maintain a pH of greater than or equal to 8.5. More preferably still, the amount of base added will maintain a pH of greater than or equal to 10.5. Two or more bases may also be used in combination.

EXAMPLES

The following examples illustrate certain embodiments of the instant invention. The purpose of these examples does not include establishing the scope of the invention which is defined in the disclosure and recited in the claims.

The meaning of abbreviations is as follows: "sec" means second(s), "min" means minute(s), "h" means hour(s), "d" means day(s), "µL" means microliter(s), "mL" means milliliter(s), "L" means liter(s), "mM" means millimolar, "M" means molar, "mmol" means millimole(s), "g" means gram(s), "kg" means kilogram(s), "lb" means pound(s), "ft" means feet and "mmHG" means millimeter of mercury.

EXAMPLE 1

Evaporation of Fermentation Broth with Addition of Base

Filter clarified fermentation broth containing 1,3-propanediol was evaporated, to achieve isolation of the 1,3-propanediol from water. Four lots of material (550 g each) were prepared by (1) adding nothing, (2) adding calcium hydroxide to adjust the pH to 12, (3) adding 50% sodium hydroxide to adjust the pH to 12, and (4) adding calcium carbonate (5 g) in excess of what would dissolve, yielding a pH of 7. Each lot was progressively evaporated in a Buchi Rotovap, first to approximately 20% of initial volume, then to approximately 5% of initial volume. Rotovap bath temperatures were decreased as evaporation progressed, starting at approximately 90° C., to approximately 80° C. at 20% volume, to approximately 70° C. at 5% volume. After reaching approximately 5% volume and 70° C., the temperature was elevated to 100° C. and held for 15 min. The lots were removed from the Rotovap flask, filtered to remove solids, and returned to the Rotovap flask at the 20% volume point, and after the final 100° C. temperature elevation, excepting the calcium carbonate lot which was only filtered at the 100° C. point. Calcium hydroxide and sodium hydroxide were added to their respective lots to maintain a pH of 10–10.5 during evaporation. Samples were withdrawn from the lots for analysis before evaporation, at 20% volume, at 5% volume, and after heating to 100° C. Samples were analyzed via gas chromatography/mass spectrometry and gas chromatography /flame ionization detection. Masses of filtered solids were also recorded.

Composition and extent of by-product formation is significantly effected by pH as well choice of base. Results are highlighted in FIG. 1. For the intermediate concentration (approximately 20% volume), calcium hydroxide shows a significant advantage over untreated material and other choices of base. For calcium hydroxide, all measured impurities are at or below the blank (untreated) level. In particular, the 3-hydroxy-propionic acid ester of 1,3-propanediol (HPS-mPDO) is nil, and the formic acid ester of 1,3-propanediol (formate-mPDO) is reduced by over an order of magnitude. Organic acids are greatly reduced for calcium and sodium hydroxide most likely do non-volatility in their ionic forms and/or precipitation.

Figure 2:
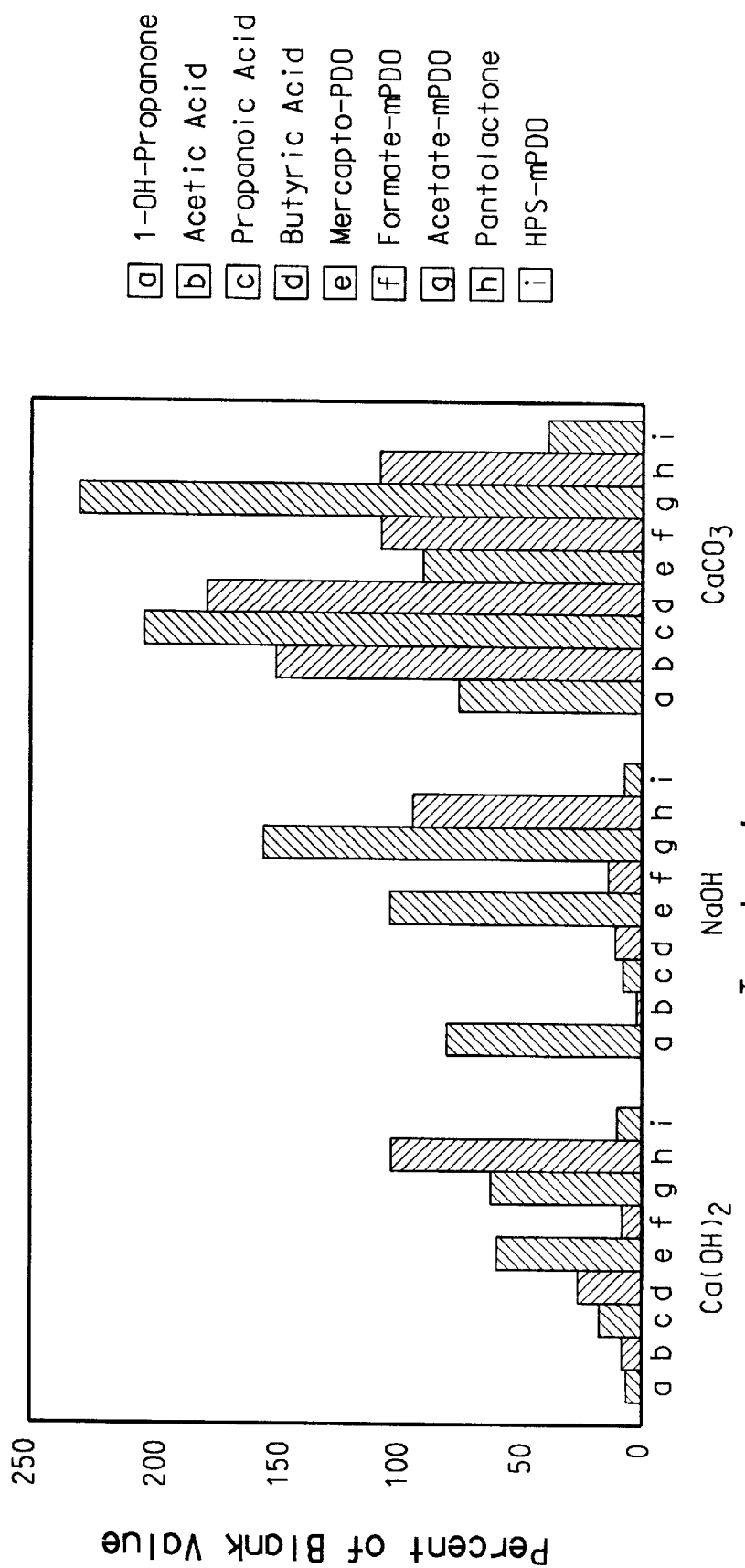
FIG. 2 illustrates an analysis of fully evaporated broth impurities via gas chromatography.

For the final concentration at 100° C. shown in FIG. 2, calcium hydroxide again shows a significant advantage over the blank, while sodium hydroxide and calcium carbonate show marginal advantage over the blank. All treatments offer abatement of HPS-mPDO formation, although a high pH (>10) appears to be advantageous over pH 7 (calcium carbonate). The same appears to be true for formate-mPDO, which may be related to HPS-mPDO chemistry rather than formic acid produced in fermentation. The acetate-mPDO is significantly lower for calcium versus sodium, indicating that calcium acetate precipitation may be occurring. Calcium hydroxide has a unique advantage in 1-hydroxypropanone levels, while no treatment appears to be effective on pantolactone.

Figure 3:
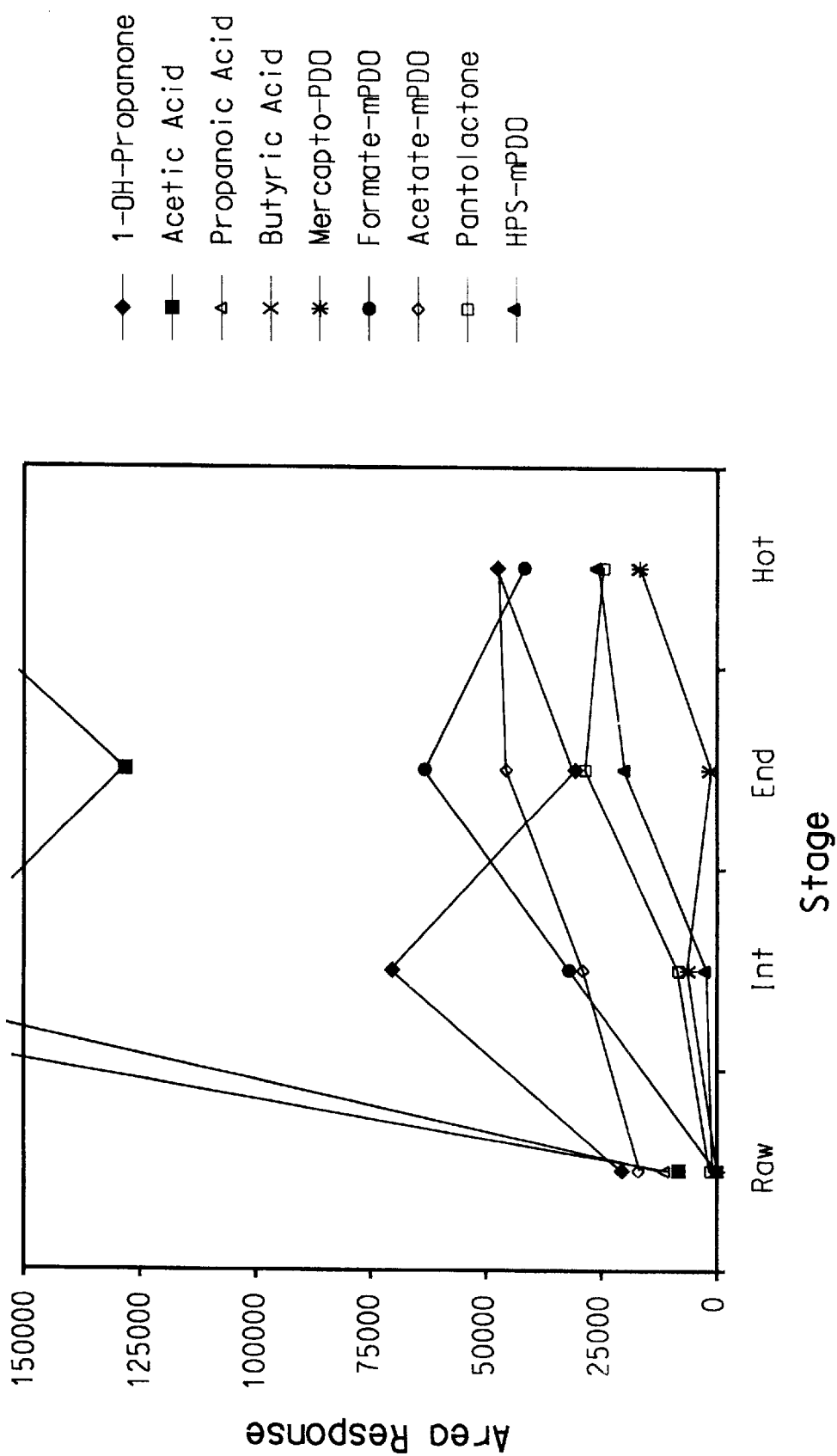
FIG. 3 illustrates gas chromatogrphy analysis of untreated broth impurities over course of evaporation.
Figure 4:
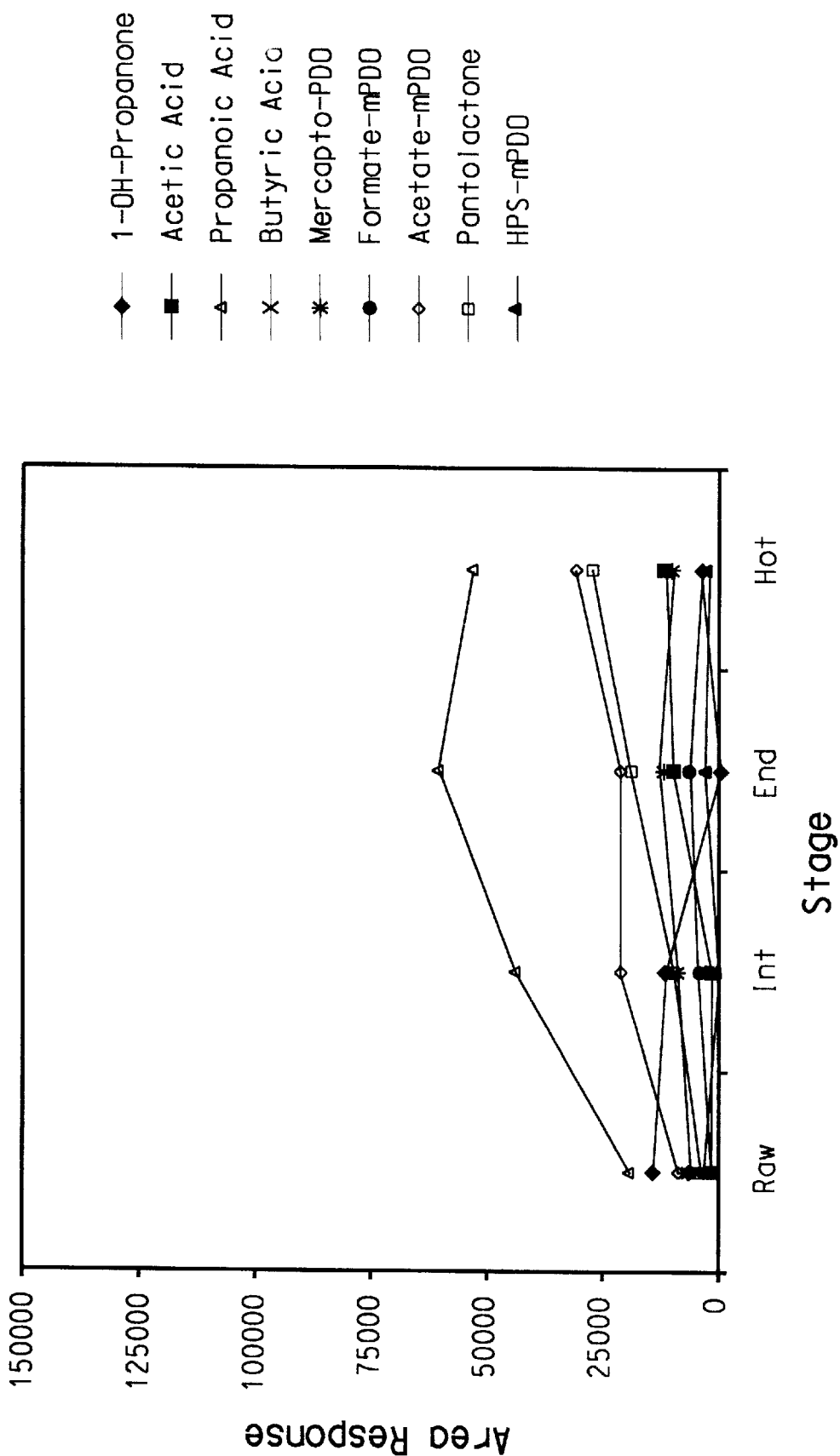
FIG. 4 illustrates gas chromatography analysis of calcium hydroxide treated broth impurities over course of evaporation.

The advantage of calcium hydroxide treatment is further illustrated by comparing the composition as evaporation progresses of the blank (FIG. 3) to that of the calcium hydroxide treated material (FIG. 4). In particular, the formation of by-products not found in clarified fermentation broth (such as HPS-mPDO) can be abated by treatment with base, more preferably by treatment with calcium hydroxide.

Figure 5:
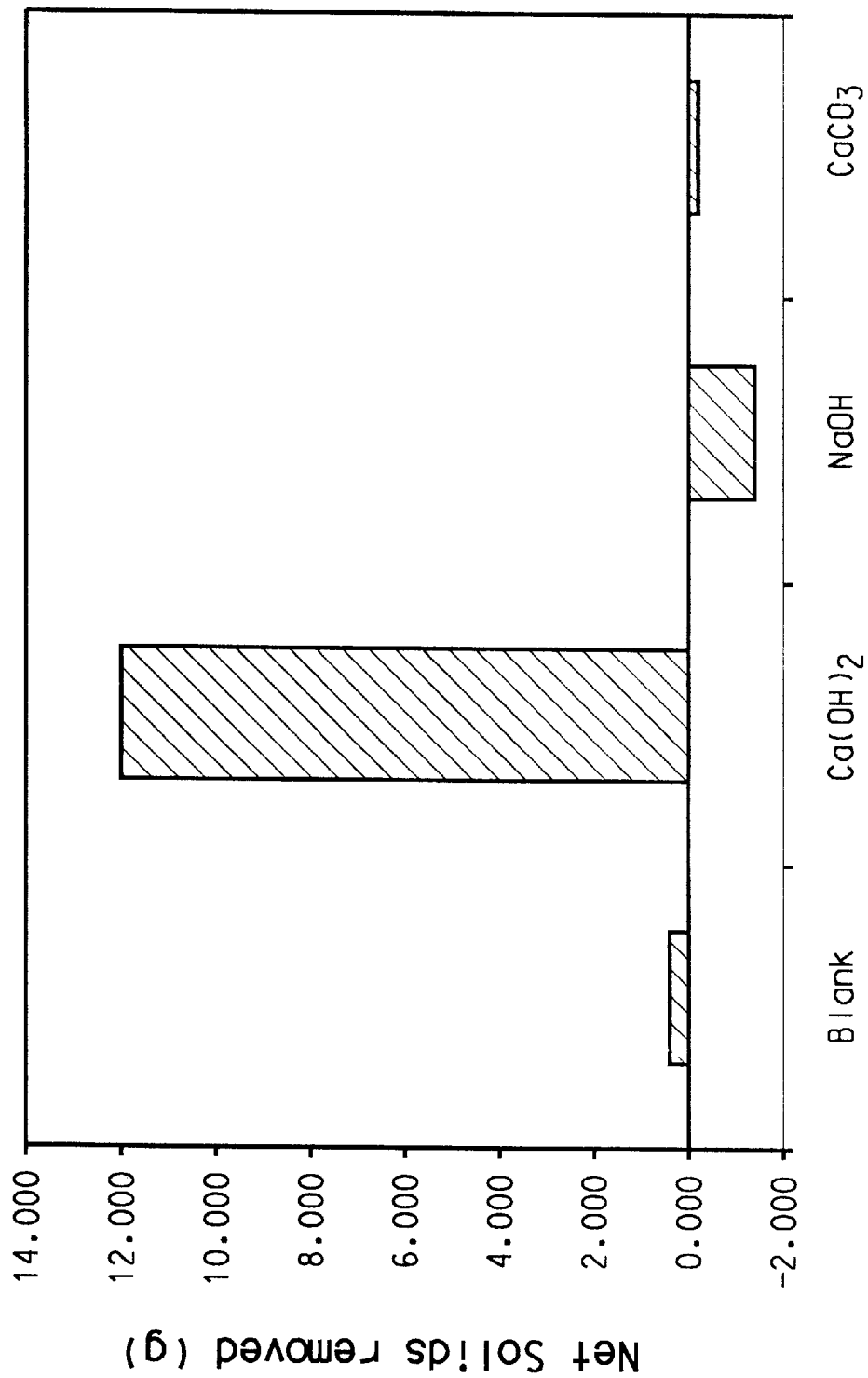
FIG. 5 illustrates net solids removed via filtration during and after evaporation.

Choice of base was found to have a significant effect on solids removed via precipitation. Calcium hydroxide appears to offer a distinct advantage over untreated material and other bases tested, in that a significant amount of dissolved solids can be removed prior to distillation. These results are illustrated in FIG. 5. As significant sample volumes were withdrawn during the runs, the value for calcium carbonate in the graph below would likely be positive if solids lost via sampling were accounted for. Only sodium hydroxide treatment, which also results in an observed viscosity much higher than the other samples, fails to at least break even in net solids removal.

This example shows that the quality of isolated 1,3-propanediol is improved via this invention. Furthermore, it shows that non-obvious, by-product formation occurs during processing of 1,3-propanediol produced via fermentation, and that this by-product formation can be reduced or eliminated with the present invention. This example also shows that the present invention can provide a significantly improved isolated product by reducing dissolved solids prior to purification by distillation.

EXAMPLE 2

Batch Distillation with Addition of Base

Previously evaporated 1,3-propanediol fermentation broth, containing approximately 20% water, was batch distilled to obtain a purified 1,3-propanediol distillate. An agitated 1 L kettle was outfitted with a Vigaro short-path distillation section, a condenser, and vacuum. Approximately 750 g of material was charged to the kettle and distilled at variable vacuum. Pressure was gradually decreased from atmospheric to 10 mmHg as the dominant distillate component changed from water to 1,3-propanediol. Distillation was continued to a kettle temperature of 187° C. and a distillate temperature of 143° C., where approximately 200 g of material remained in the kettle. Samples of the distillate were taken at intervals for analysis by gas chromatography.

A second batch of previously evaporated 1,3-propanediol fermentation broth, also containing approximately 20% water, was batch distilled as described above immediately prior with the following changes. The pH was adjusted to 8.5 before starting with 50% NaOH from an initial pH of 5.5. The pH of the kettle sample taken at the first distillate cut was 5.6, while the distillate was at 10.7 and smelled of ammonia. An additional 20 g of NaOH was added to the kettle. The next sample kettle sample taken had a pH of 10.6, while the distillate pH was 9.9. Distillation was continued to a kettle temperature of 235° C. and a distillate temperature of 130° C., where approximately 200 g of material remained in the kettle.

Figure 6:
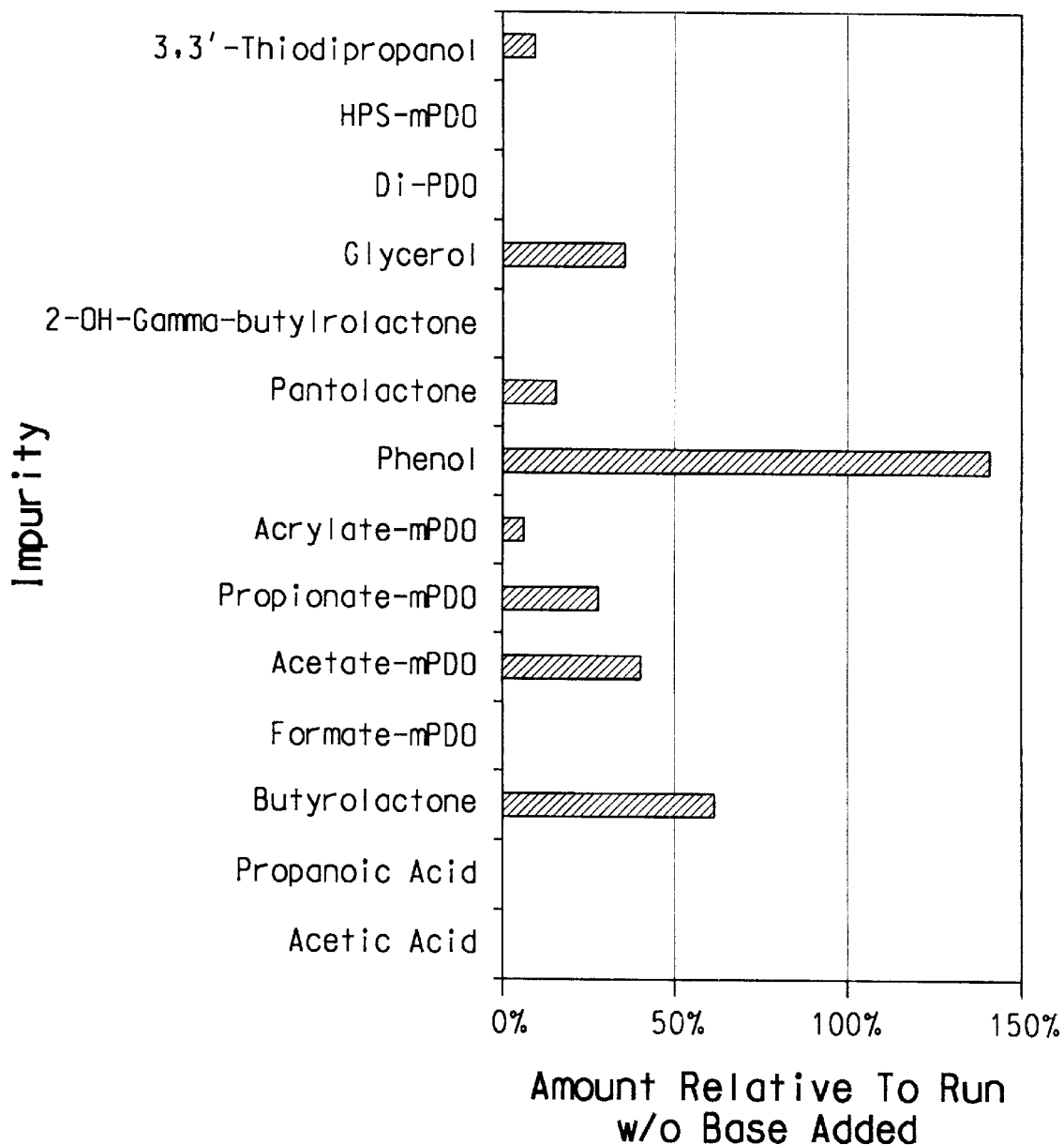
FIG. 6 illustrates gas chromatography analysis of distillate samples.

Distillation at high pH conditions eliminated the formation of HPS-mPDO and acrylate-mPDO which was found to be significant without base addition. Several other impurities were also significantly reduced by addition of base including acetate-mPDO, formate-mPDO, butyrolactone and pantolactone. A comparison of distillate cut number 5 for each batch is shown in FIG. 6 which illustrates the reduction in by-products due to addition of base. For the batch with base added, a cut purity of 99.5% was obtained, while the same operation without base produced no higher than 97% 1,3-propanediol due to presence of the esters and lactones.

The advantage of base addition is furthermore exemplified by yields. The yield of 1,3-propanediol recovered in distillate samples was 78% for the batch without base addition, while a yield of 95% was obtained with base addition. Kettle and distillate samples near the end of the without-base run contained large amounts of the esters, lactones, and other unidentified products. Only an additional 1% of the 1,3-propanediol fed was accounted for in the material left in the kettle. The yield losses are believed to be due to reactions which can be abated by addition of base.

This example shows that the quality of isolated 1,3-propanediol is improved via this invention. Furthermore, it shows that non-obvious by-product formation occurs during processing of 1,3-propanediol produced via fermentation, and that said formation can be reduced or eliminated with the present invention. This example also shows that product yield can be significantly improved by reducing formation of 1,3-propanediol by-products.

EXAMPLE 3

Continuous Distillation with Addition of Base

Previously evaporated 1,3-propanediol fermentation broth with a pH of 5.4, containing approximately 60% water, was continuously distilled to obtain purified 1,3-propanediol. The material was fed to a 2" Oldershaw vacuum distillation column where the majority of the 1,3-propanediol was taken overhead along with lighter components including water. A smaller amount of 1,3-propanediol and heavier components including dissolved solids comprised the bottoms stream. The column had 35 trays and operated at an average reboiler temperature of 170° C. The collected distillate which had a pH of 5.0, was then continuously fed to the same column, taking water overhead, and producing a de-watered 1,3-propanediol as the bottoms stream. The column again had 35 trays and operated at an average reboiler temperature of 165° C. The de-watered 1,3-propanediol represents a crude product which is suitable for final purification by distillation to remove close boiling impurities.

A second batch of evaporated 1,3-propanediol fermentation broth, containing approximately 20% water, was continuously distilled to obtain purified 1,3-propanediol. Prior to distillation, the pH was adjusted to 10.5 with sodium hydroxide. The material was continuously fed to a 2" Oldershaw vacuum distillation column where water was taken overhead, and 1,3-propanediol with heavier components including dissolved solids comprised the bottoms stream. The column had 10 trays and operated at an average reboiler temperature of 145° C. The collected bottoms product had a pH of 8.8. This material was then continuously fed to the same column where the majority of the 1,3-propanediol was taken overhead along with lighter components. A smaller amount of 1,3-propanediol and heavier components including dissolved solids comprised the bottoms stream. This step was performed in three lots, each with a different method. Lot 1 had no pH adjustment and an average reboiler temperature of 195° C. Lot 2 had no pH adjustment and an average reboiler temperature of 170° C. Lot 3 was adjusted to pH 12.5 prior to feeding and had an average reboiler temperature of 175° C. Each of the three lots represents a crude product which is suitable for final purification by distillation to remove close boiling impurities.

The color of the crude 1,3-propanediol products made without pH adjustment and the three lots made with pH adjustment was compared. Color was measured using the Gardner Color Scale (Gardner Liquid Color Standard Comparator, ASTM D 1544). Higher color numbers represent more color. Final 1,3-propanediol product suitable for polymer applications must be water-white, translating to a Gardner color of zero. Table 1 illustrates the advantage of base addition prior to distillation. Distillation of material without base adjustment, and therefore under acidic conditions, produced the most colored material. While multiple experimental variables were changed, operation at reboiler pH $\geq 8.5$ significantly improved color. Adjustment of the second column feed pH from 8.8 to 12.5 also resulted in a significant improvement in color. This improvement is in spite of a 5° C. increase in reboiler temperature. It is evident by comparing Lots 1 and 2 that increased temperature results in increased color. The results indicate that product color can be improved by increasing pH by base addition. Furthermore, the results indicate that a feed pH $\geq 10.5$ is preferable, with a feed pH $\geq 12.5$ being more preferable. As the specific composition of the color bodies or the color bodies formed during distillation is not known, the improvement in color as a function of pH could not be expected a priori.

This example shows that the present invention can significantly improve the color of 1,3-propanediol produced from fermentation broth. Color is an important product specification that significantly influences product utility and value. Furthermore, this example shows that color improvement increases with pH, and that the effect of pH can be more significant than the effect of temperature in a distillation device recognized in the art as scalable to commercial operation.

TABLE 1

| CRUDE 1,3-PROPANEDIOL | pH $1^{ST}$ FEED | pH $2^{ND}$ FEED | GARDNER COLOR |
|---|---|---|---|
| No base adjustment | 5.4 | 5.0 | 18 |
| Adjusted, Lot 1 | 10.5 | 8.8 | 12 |
| Adjusted, Lot 2 | 10.5 | 8.8 | 9 |
| Adjusted, Lot 3 | 10.5 | 12.5 | 5 |

What is claimed is:

1. A process for the isolation of 1,3-propanediol from a fermentation broth comprising the steps of:
   (a) adding base to the fermentation broth to raise the pH above 7.0; and
   (b) isolating 1,3-propanediol from the fermentation broth of step 1(a) by evaporating, distilling, filtering, extracting, or crystallizing.

2. The process of claim 1 further comprising step (c) removing precipitated solids from the product of step (b) by 1) filtering or centrifuging, or 2) vacuum distilling.

* * * * *